United States Patent [19]

Turconi

[11] 4,347,373
[45] Aug. 31, 1982

[54] DERIVATIVES OF 4-METHYL-5-[(2-AMINOETHYL)-THIOMETHYL]-IMIDAZOLE

[76] Inventor: Franco Turconi, Via S. Dalmazio 14, 21047 Saronno (Varese), Italy

[21] Appl. No.: 241,563

[22] Filed: Mar. 9, 1981

[30] Foreign Application Priority Data

Mar. 18, 1980 [IT] Italy ................................ 20734 A/80

[51] Int. Cl.³ .................. C07D 233/64; C07D 403/12; C07D 409/12
[52] U.S. Cl. ................................ 548/336; 260/326.1; 260/326.13 A; 548/342; 549/72; 562/460; 562/466; 562/469; 562/477; 562/492; 562/496
[58] Field of Search .............................. 548/342, 336; 424/273 R

[56] References Cited

U.S. PATENT DOCUMENTS 2,301,532  11/1942  Fell ...................................... 548/342

FOREIGN PATENT DOCUMENTS 233730  8/1944  Switzerland ........................ 548/342

OTHER PUBLICATIONS

March, J., *Advanced Organic Chemistry*, McGraw Hill, New York, 1968, p. 335.

Primary Examiner—Richard A. Schwartz
Attorney, Agent, or Firm—Steinberg & Raskin

[57] ABSTRACT

This invention relates to a series of compounds having therapeutic activity, consisting of the derivatives obtained by reacting 4-methyl-5-[(2-aminoethyl)-thiomethyl]-imidazole with non-steroidal, traditional, antiinflammatory agents. The derivatives are carboxamides of formula

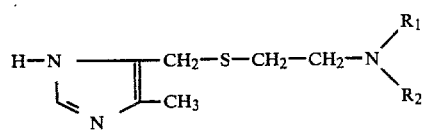

wherein $R_1 = H$; $-CH_3$; $-C_2H_5$; and

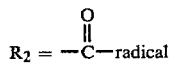

of the antiinflammatory agents, i.e. the acylic radical of the antiinflammatory acid, or

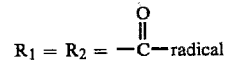

of the antiinflammatory acid and the corresponding physiologically acceptable salts on the imidazole ring.

10 Claims, No Drawings

DERIVATIVES OF 4-METHYL-5-[(2-AMINOETHYL)-THIOMETHYL]-IMIDAZOLE

The present invention relates to a series of novel derivatives of 4-methyl-5][(2-aminoethyl)-thiomethyl]-imidazole having antiinflammatory, antipyretic and analgesic activity, low collateral gastrodamaging effect and long-acting antiinflammatory action. Such compounds are obtained by bonding the above-mentioned imidazole moiety with known molecules, having those activities but also a remarkable and well-known collateral gastrodamaging effect and a short antiinflammatory action which is usually carried out with a maximum during the first hour after the administration followed by a rapid decrease of plasma levels.

Surprisingly, it was found that bonding 4-methyl-=-](2-aminoethyl)-thiomethyl]-imidazole with known compounds belonging to the class of non-steroidal antiinflammatory agents, such as indomethacin, diflunisal, flurbiprofen, indroprofen, 4-diphenylyl-ethyl-acetic acid, ibuprofen, naproxen, suprofen (i.e. ](thenoyl-2)-4-phenyl]2-propionyl acid), ketoprofen, salicylic acid, all of which are acid, carboxamides are obtained having the therapeutic activity of the parent compound with a more prolonged effect and with a substantially decreased gastrodamaging action.

The derivatives of the present invention are the amides of formula:

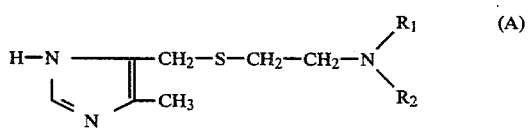

wherein $R_1 = $ —H; —CH$_3$; —C$_2$H$_5$ and $R_2 = $ acylic radical of the antiinflammatory acid or $R_1 = R_2 = $ acylic radical of the antiinflammatory acid; as well as the salts on the imidazole ring of such amides with physiologically acceptable acids.

The wording acylic radical means the radical of a carboxylic acid in which the hydroxy group of the carboxyl was deleted.

The amides are obtained by reacting the corresponding active derivative of the non-steroidal antiinflammatory acid, for example the acyl chloride, with the base, namely 4-methyl-5-](2-aminoethyl)-thiomethyl]-imidazole or with its hydrochloride.

In order that the present invention be more clearly understood, some unrestrictive exemplary embodiments of the invention will now be described.

EXAMPLE 1

Derivative of formula (A) wherein $R_1 = H$ and

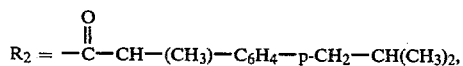

i.e. 2-(p-isobutylphenyl)propionamide of 4-methyl-5](2-aminoethyl)-thiomethyl)]imidazole.

(a) Preparation of the acyl chloride of the 2-(p-isobutylphenyl) propionic acid (ibuprofen)

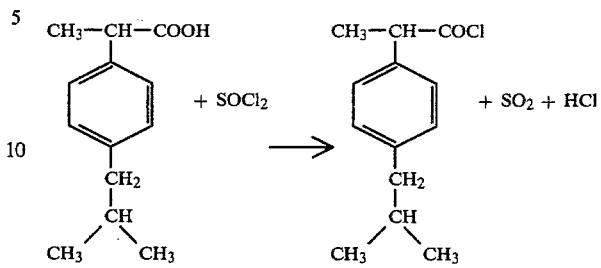

12 l of chloroform and 2.9 l of thionyl chloride (equivalent to about 39.97 moles) were poured into a glass-flask. 5 kg of 2-(p-isobutylphenyl) propionic acid were added to the solution. The acid dissolved while the temperature fell.

The solution was warmed up to 20°-30° C. gradually and at this point gaseous SO$_2$ and H Cl began to evolve. Heating was continued gradually checkingg the gaseous evolution in such a way as to avoid an excessive evaporation of the solvent. The temperature of the reaction mixture was raised up to 50°-63° C. by this way and the solvent was refluxed for about an hour. At this point the reaction was completed as the gas evolution was stopped. The mixture was concentrated under vacuum in order to remove chloroform and excess thionyl chloride completely. For this purpose the oily, steaming residue was dissolved with 1000 ml of chloroform, the resulting solution was concentrated under vacuum until the solvent and thionyl chloride were removed. The oily, steaming, cognac coloured residue was constituted by the chloride of 2-(p-isobutylphenyl) propionic acid which was reacted as such. Yield: about 5.440 kg (100% of the theoretical amount calculated on the raw material).

(b) Preparation of the amide of 4-methyl-5-[(2-aminoethyl)-thiomethyl]-imidazole with 2-(p-isobutylphenyl)-propionic acid Two alternative routes can be followed for this preparation:

(B 1) First method

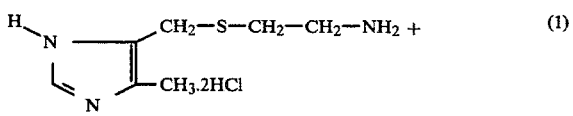

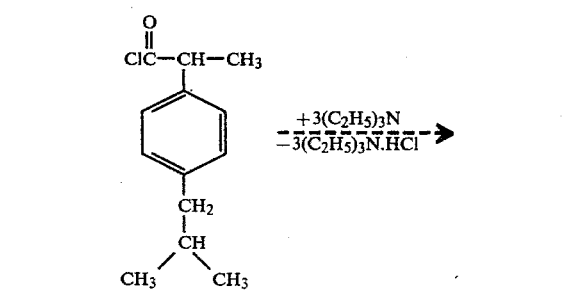

-continued

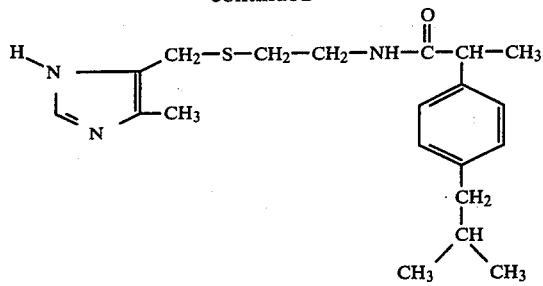

1000 ml of chloroform (also other solvents, provided that they are inert to acyl chlorides in these conditions, can be used, as well as benzene, toluene, ethers, chlorinated solvents, tertiary amines and other solvents) and 240 g (0.983 moles) of 4-methyl-5-[(2-aminoethyl)-thiomethyl]-imidazole dihydrochloride were poured into a glass-flask.

316 g (about 3.12 moles) of triethylamine were added gradually under stirring and at room temperature; reaction took place and the crystalline compound changed to a suspension. The reaction was exothermic.

Alternatively other tertiary amines may be used, for example pyridine. Then 220 g (about 0.98 moles) of 2-(p-isobutylphenyl) propionic acid chloride dissolved in 500 ml of chloroform were added gradually, while stirring and keeping the reaction temperature at $10°÷40°$ C. by cooling with water externally. Upon completion of addition, the solution was kept at room temperature for 1 hour: thereafter it was refluxed for 30 minutes. At this point the reaction was completed and the mixture was worked up. It was washed twice with water and twice with sodium bicarbonate solution. The organic phase was dried on sodium sulphate and then evaporated to dryness under reduced pressure. The residue was dissolved in 500 ml of ethanol and the solution thus obtained was poured into 9 l of aqueous sodium carbonate solution under vigorous stirring.

After one hour 500 ml of acetone and after about additional 60 minutes 100 ml of ammonium hydroxide were added: the solution was stirred until crystallization was completed. The precipitate was filtered, washed with water and dried under ventilation. The product was purified by suspension in petroleum ether and diethyl ether and there was crystallized from methylisobutylketone. Yield of the purified product: 170 gr.

The resulting, crystallized product having molecular weight 359.528 presented the following elementary analysis:

|   | Calculated % | Found % |
|---|---|---|
| C | 240.220/M.W. = 6.81 | 66.55 |
| H | 29.229/M.W. = 8.12 | 8.05 |
| N | 42.020/M.W. = 1.68 | 11.53 |

The obtained, crystallized product appears as a white, practically odourless, bitter, microcrystalline powder; it melts at about $117°-120°$ C., is practically insoluble in water and petroleum ether, whereas it is soluble in methanol, ethanol, tetrahydrofuran, acetone and chloroform.

On thin layer chromatography (silica gel 254 Merck; chloroform-methanol-ammonium hydroxide 40:10:0.5 as eluent) it has Rf about 0.70.

At the spectrophotometric analysis the compound shows the following characteristics:

I.R. spectrum shows a peak at 1670 $cm^{-1}(c_1=0$ amid. In the present and in the following examples, H—NMR spectra were recorded on EM-390 90 MHz, or EM-360 60 MHz, or XL-100 100 MHz (NMR spectrometer). Values are stated in ppm ($\delta$), downfield from tetramethylsilane as internal reference standard. The following abbreviations are used in reporting the N.M.R. data: s=singlet; d=doublet; t=triplet; q=quartet; m=multiplet.

As far as the compound of present example is concerned (90 MHz) spectrum (CD $Cl_3,\delta$) shows the following peaks: 0.87 (d, 6H, $CH_3$); 1.46 (d, 3H, $CH_3$); 1.66–2 (m, 1H, CH); 2.18 (s, 3H, $CH_3$); 2.42–2.57 (m, 4H, $CH_2$); 3.37 (q, 2H, $CH_2$); 3.64 (s, 2H, $CH_2$); 7–7,35 (q, 4H, aromatic H); 7.67 s, 1H, aromatic H); 9.08 (s, 2H, NH).

The same compound, namely the amide of formula (1), can be obtained also according to the following method, i.e., in general terms, by reacting the acyl chloride of the 2-(p-isobutyl-phenyl) propionic acid with 4-methyl-5-[(2-aminoethyl)-thiomethyl]imidazole bis-hydrochloride aqueous solution, at low temperature and under stirring in presence of sodium hydroxide or alkaline carbonates according to the following reaction scheme:

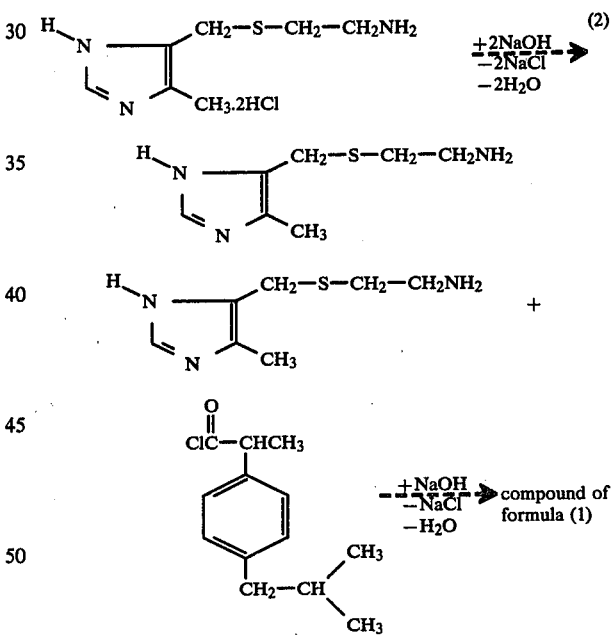

This second way of preparing the compound of formula (1) is expressed numerically as follows:

240 g of 4-methyl-5-[(2-aminoethyl)-thiomethyl]-imidazole bis-hydrochloride (about 0.98 moles) were dissolved in 400 ml of water; separately 80 gr of NaOH (2 moles) were dissolved in 120 ml of iced water. The two solutions were mixed and the compound of formula (2), namely 4-methyl-5-[(2-aminoethyl)-thiomethyl]-imidazole base, was set free.

Separately, further 40 gr of NaOH were dissolved in 80 ml of iced water.

Ice was added to the solution of the compound (2) above obtained and the NaOH solution previously prepared was added slowly drop by drop under vigorous stirring at the same time with 240 g of the acyl chloride of the 2-(p-isobutylphenyl) propionic acid. During the reaction the temperature was kept low by adding ice in pieces. At the end of the addition stirring was continued for some hours at room temperature. The reaction mixture was extracted with 2 l of chloroform and the organic phase was evaporated to dryness under reduced pressure. The residue was dissolved in diluted hydrochloric acid: the solution was filtered and then the compound (1) was precipitated by adding ammonium hydroxide. The raw material was purified as above described according to method B 1.

EXAMPLE 2

The compound of formula (1)—and in general all the derivatives of formula (A)—can be salified with mineral and also organic acids. Particularly such compound (1) is salified here with fumaric acid, as in the following scheme, in order to obtain the corresponding salt:

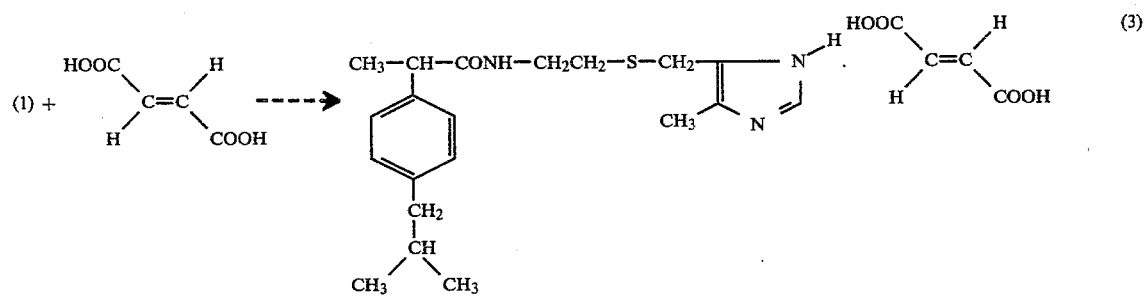

72 g of compound (1) were reacted with 23.2 g of fumaric acid in 500 ml of acetone (or alcohols or ketones generally) at the boiling temperature. On cooling the product crystallized, was filtered and dried under reduced pressure. The product was recystallized from acetone containing little ethanol. Yield: 60 g. The obtained compound appears as a white, practically odourless, bitter, slightly acid, microcrystalline powder, having melting point 102°–105° C.; it is practically insoluble in acetone, whereas it is soluble in ethanol, very little soluble in cold water, more soluble in warm water (pH of the solution about 4.5). Its molecular weight is 475.601 and on thin layer chromatography (silica gel 254 Merck; chloroform methanolammonium hydroxide 40:10:0.5 as eluent) it shows two spots: one of the base (formula I) having Rf about 0.7, the second of fumaric acid, almost at the starting point, having therefore Rf=0.0.

| Elementary analysis | Calculated % | Found % |
|---|---|---|
| C | 60.61 | 60.29 |
| H | 6.99 | 6.71 |
| N | 8.83 | 8.74 |

NMR (100 MHz)spectrum (DMSO,$\delta$): 0.86 (d, 6H, CH$_3$); 1.33 (d 3H, CH$_3$); 1.6–2 (m, 1H, CH); 2.16 (s, 3H, CH$_3$); 2.35–2.62 (m, 4H, CH$_2$); 3.24 (q, 2H, CH$_2$); 3.45–3.70 (m, 1H,CH); 3.7 (s, 2H, CH$_2$); 6.68 (s,2H, CH=CH); 7–7.35 (q, 4H, aromatic H); 7.90 (s, 1H, aromatic H); 8.14 (t, 1H, NH).

In imitation of the methods described in Example 1 and Example 2 (where salts are involved) the following compounds have been obtained:

(a) The compound of formula (A) in which R$_1$=H and R$_2$=acylic radical of (+) 6-methoxy-$\alpha$-methyl-2-naphthalen-acetic acid (naproxen), i.e. the radical: (+) 6-methoxy-$\alpha$-methyl-2-naphthalen-acetyl.

The compound which is obtained has therefore formula:

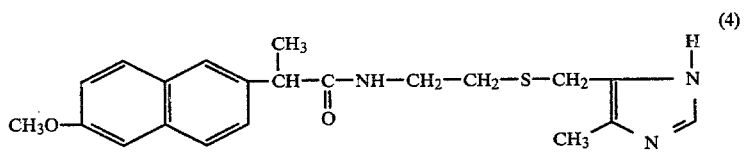

Such compound appears as white crystals (from acetone/ethanol); it has melting point 147°–149° C.; it is odourless; it has general formula C$_{21}$H$_{25}$N$_3$O$_2$S and molecular weight 383.507. On thin layer chromatography (carried out as described in the previous examples) it has Rf about 0.70. The compound is soluble in methanol, ethanol and isopropyl alcohol, slightly soluble in hydrochloric acid, very slightly soluble in acetone and practically insoluble in water, benzene and ethyl acetate.

U.V. spectrum shows peaks at $\lambda$ max=233 m$\mu$; 262 m$\mu$; 272 m$\mu$.

I.R. spectrum shows a peak at 1640 cm$^{-1}$ (C=O amidic).

N.M.R. (90 MHz) spectrum (DMSO,$\delta$): 1.42 (d, 3H, CH$_3$); 2.10 (s, 3H, CH$_3$); 2.4–2.7 (m, 2H, CH$_2$); 3.15–3.45 (m, 2H, CH$_2$); 3.63 (s, 2H, CH$_2$); 3.88 (s, 3H, O—CH$_3$); 3.65–3.85 (m, 1H, CH); 7.1–7.9 (m, 7H, aromatic H); 8.23 (m, 1H, NH).

| Elementary analysis | Calculated % | Found % |
|---|---|---|
| C | 65.76 | 65.46 |
| H | 6.57 | 6.66 |
| N | 10.95 | 10.64 |

The compound of formula (4) above mentioned, reacted with fumaric acid according to the method described in Example 2, provides the following compound:

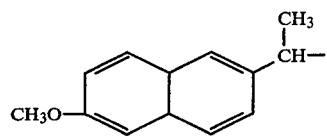
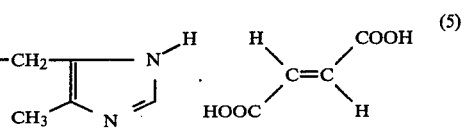

(5)

The compound has formula $C_{25}H_{29}O_6N_3S$ and molecular weight 499.580.

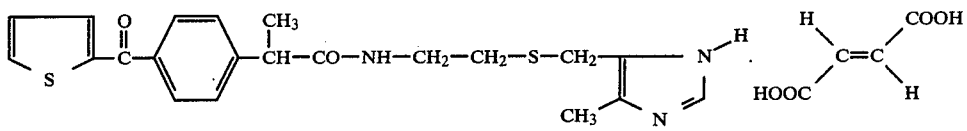

It appears as white crystals (from ethanol or acetone-ethanol); it has melting point 149°–150° C., is odourless and bitter. On thin layer chromatography, carried out as above described, it shows two spots: one of the compound of formula (4) having Rf about 0.70, the second of fumaric acid, at the starting point, having Rf=0.0.

The compound is very slightly soluble in cold water, whereas is soluble in warm water (pH of the solution about 4.5); it is soluble in methanol, practically insoluble in acetone and benzene; insoluble in diethyl ether; slightly soluble in cold ethanol whereas it is soluble in warm ethanol.

| Elementary analysis | Calculated % | Found % |
|---|---|---|
| C | 60.10 | 59.92 |
| H | 5.85 | 5.79 |
| N | 8.41 | 8.50 |

N.M.R. (100 MHz) spectrum (DMSO,δ): 1.42 (d, 3H, CH$_3$); 2.12 (s, 3H, CH$_3$); 2.4–2.65 (m, 2H, CH$_2$); 3.12–3.40 (q, 2H, CH$_2$); 3.65 (s, 2H, CH$_2$); 3.65–3.85 (m, 1H, CH); 3.88 (s, 3H, O—CH$_3$); 6.69 (s, 2H, CH=CH); 7.1–7.9 (m, 7H, aromatic H); 8.18 (t, 1H, NH); 9.52 (m, 3H, NH, COOH).

(b) The compound of formula (A) in which R$_1$=H and R$_2$=[(thenoyl-2)-4-phenyl]2-propionyl (acylic radical of suprofen).

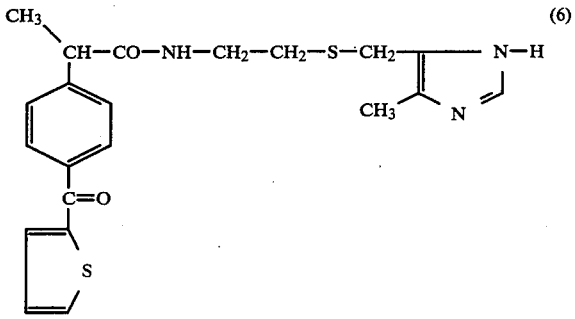

The compound (6) appears as a white gum, insoluble in water, soluble enough in common organic solvents.

Compound (6) is salified with fumaric acid as in example 2 and the salt is obtained. It has general formula $C_{25}H_{27}O_6N_3S_2$ and molecular weight 529.624. It appears as white crystals (from acetone ethanol); has melting point about 146.5°–148° C.; is odourless, bitter and slightly acid. On thin layer chromatography, carried out as above described, it shows one spot corresponding to compound (6) having Rf about 0.63 and a second spot corresponding to fumaric acid, at the starting point, having Rf=0.00.

The compound is slightly soluble in cold water, whereas is soluble in warm water (pH of the solution about 4.5–5). It is also slightly soluble in alcohols whereas it is soluble in warm alcohols. It is soluble in ethanol containing a little water; it is insoluble in acetone and ethyl ether.

| Elementary analysis | Calculated % | Found % |
|---|---|---|
| C | 59.69 | 56.85 |
| H | 5.13 | 5.29 |
| N | 7.93 | 7.71 |

(c) Compound of formula (A) wherein R$_1$=H and R$_2$=2 (3-benzoilphenyl)-propionyl (from ketoprofen), namely:

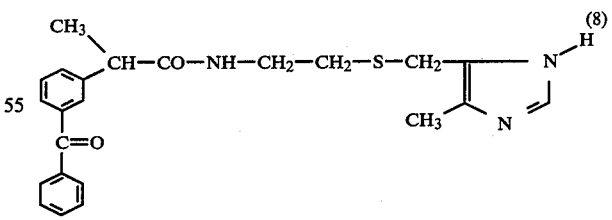

Compound (8), after purification, appears as white, odourless microcrystals, having melting point 141°–144° C. It has general formula $C_{23}H_{25}N_3O_2S$ and molecular weight 407.529. It is soluble in methanol and ethanol, slightly soluble in chloroform and acetone, practically insoluble in water. The compound of formula (8) is salified with fumaric acid as in Example 2 and the salt:

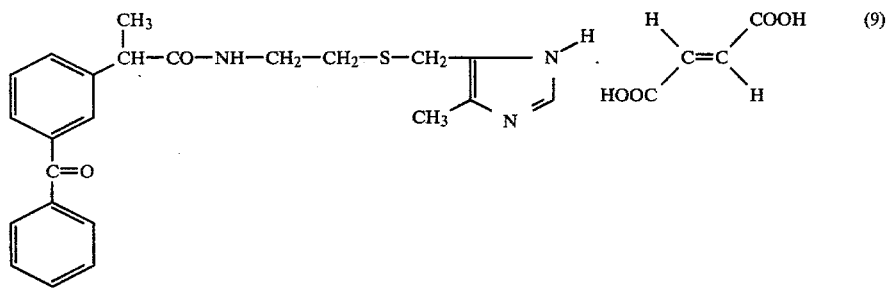

is obtained.

The compound (9) has general formula $C_{27}H_{29}N_3O_6S$ and molecular weight 523.602. It appears as white (from acetone-ethanol), odourless, bitter and slightly acid crystals having melting point 97°-100° C.

On thin layer chromatography, carried out as above described, it shows two spots: one corresponding to compound (8) having Rf about 0.5, the second corresponding to fumaric acid, at the starting point, having Rf=0.0.

The compound is very slightly soluble in water (pH of the suspension about 4.5) and shows a tendency to hydrolysis. It is soluble in methanol, very slightly soluble in acteone, insoluble in petroleum ether and practically insoluble in chloroform.

| Elementary analysis | Calculated % | Found % |
|---|---|---|
| C | 61.93 | 62.05 |
| H | 5.58 | 5.71 |
| N | 8.02 | 7.90 |

N.M.R. (100 MHz) spectrum (CDCl3DMSO,δ): 1.51 (d, 3H, CH3); 2.19 (s, 3H, CH3); 2.5-2.7 (m, 2H, CH2); 3.4 (q, 2H, CH2); 3.62 (s, 2H, CH2); 3.6-3.8 (m, 1H, CH); 6.8 (s, 2H, CH=CH); 7.35-7.9 (m, 10H, aromatic H).

(d) Compound of formula (A) wherein $R_1$=H and $R_2$=2-hydroxy-benzoil (acylic radical of salicylic acid).

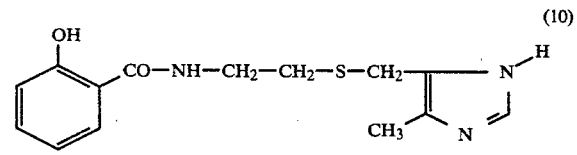

The compound has general formula $C_{14}H_{17}N_3O_2S$ and molecular weight 291.367. It appears as bright, white crystals (from ethanol) having melting point 160°-163° C.; the compound is odourless and almost tasteless.

On thin layer chromatography, carried out as above described, it shows Rf about 0.64.

The compound is soluble in hydrochloric acid 0.1 N, very slightly soluble in ethanol and acetone, practically insoluble in water and chloroform, insoluble in benzene and petroleum ether.

| Elementary analysis | Calculated % | Found % |
|---|---|---|
| C | 57.71 | 57.50 |
| H | 5.88 | 5.71 |
| N | 14.42 | 14.34. |

N.M.R. (60 MHz) spectrum (DMSO,δ): 2.19 (s, 3H, CH3); 2.45-2.9 (m, 2H, CH2); 3.3-3.7 (m, 2H, CH2); 3.72 (s, 2H, CH2); 6.7-8.2 (m, 5H, aromatic H); 9-9.3 (m, 1H, NH); 11.2-11.8 (m, 2H, NH, —OH).

The compound of formula (10) is salified with fumaric acid, as per Example II, providing:

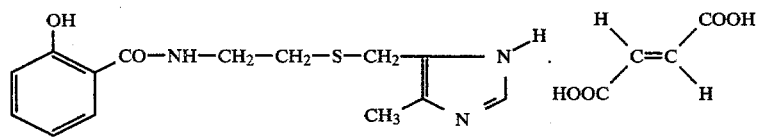

The compound has general formula $C_{18}H_{21}N_3O_6S$ and molecular weight 407.440. It appears as white crystals (from ethanol) having melting point 159°-160° C.

On thin layer chromatography, carried out as above described, it shows two spots: one corresponding to the compound of formula (10) having Rf about 0.64 and the second to fumaric acid at Rf=0.0 (starting point).

The salt is soluble in lukewarm water (pH solution about 4-4.5), slightly soluble in ethanol.

| Elementary analysis | Calculated % | Found % |
|---|---|---|
| C | 53.06 | 52.92 |
| H | 5.19 | 5.15 |
| N | 10.31 | 10.30. |

Compound of formula (10) reacted with hydrogen chloride in acetone and in alcohol provides the corresponding hydrochloride:

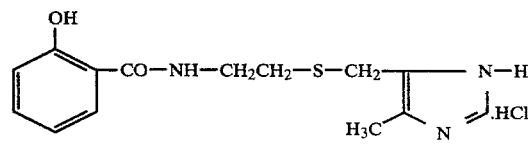

The hydrochloride has general formula $C_{14}H_{18}N_3O_2S\,Cl$, and molecular weight 327.82. It appears as white crystals (from acetone-ethanol) having melting point 194°-196° C. with decomposition; it is soluble in water (7% solution, with pH about 5.5), slightly soluble in ethanol, insoluble in acetone and diethyl ether.

| Elementary analysis | Calculated % | Found % |
| --- | --- | --- |
| C | 51.29 | 50.99 |
| H | 5.53 | 5.44 |
| N | 12.81 | 12.78 |

(e) Product of formula (A) wherein $R_1=H$, $R_2=$ 4-diphenylyl ethyl-acetyl (aromatic radical of 4-diphenylethylacetic acid).

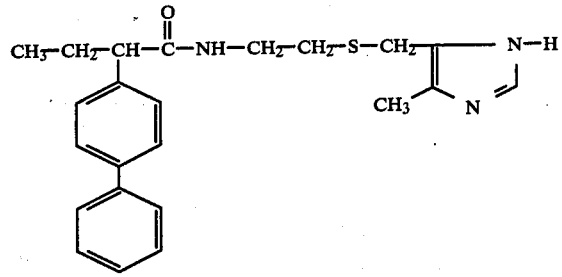

The compound has general formula $C_{23}H_{27}N_3OS$ and molecular weight 393.545. It appears as white, odourless microcrystals having melting point 185°–188° C.

On thin layer chromatography, carried out as above described, it shows Rf about 0.5.

The compound is soluble in dimethylformamide; slightly soluble in methanol, ethanol, isopropanol, and in diluted hydrochloric acid; very slightly soluble in acetone and practically insoluble in water.

| Elementary analysis | Calculated % | Found % |
| --- | --- | --- |
| C | 70.19 | 69.80 |
| H | 6.91 | 6.87 |
| N | 10.76 | 10.51 |

Compound of formula (13) is salified with fumaric acid as in Example 2 and the salt:

is obtained.

The compound has general formula $C_{27}H_{31}N_3O_5S$ and molecular weight 509.619. It appears as white, odourless, microcrystalline powder, having melting point 155°–157° C.

On thin layer chromatography, carried out as above described, it shows two spots: one corresponding to compound (13) having Rf about 0.52, the second corresponding to fumaric acid, at the starting point, having Rf about $=0.0$. The salt is soluble in methanol, slightly soluble in ethanol, very slightly soluble in water, insoluble in acetone and chloroform. The suspension has a pH about 4.5.

| Elementary analysis | Calculated % | Found % |
| --- | --- | --- |
| C | 63.63 | 63.47 |
| H | 6.13 | 6.22 |
| N | 8.24 | 8.15 |

(f) Compound of formula (A) wherein $R_1=H$ and $R_2=$ 1-(p-chorobenzoil)-2-methyl-5-methoxy-3-indolylacetyl (acylic radical of 1-(p-chlorobenzoil)-2-methyl-5-methoxy-3-indolylyl-acetic acid) indomethacin.

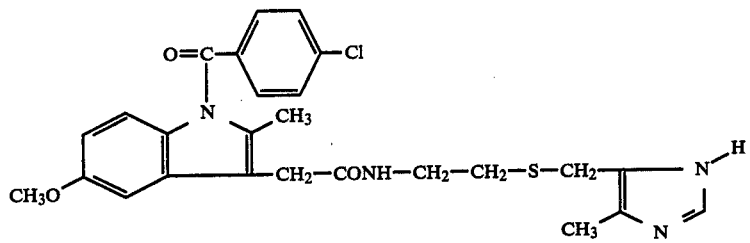

The compound has general formula $C_{26}H_{27}N_4O_3Cl\,S$ and molecular weight 511.037.

It appears as cream-coloured microcrystalline powder having melting point 163°–166° C. with decomposition.

On thin layer chromatography carried out as above described, it shows one spot having Rf about 0.56.

The compound is soluble in N,N-dimethylformamide, fairly soluble in ethanol 95° and in moist acetone, slightly soluble in dioxane, very slightly soluble in chloroform, acetone and hydrochloric acid, practically insoluble in water.

| Elementary analysis | Calculated % | Found % |
| --- | --- | --- |
| C | 61.10 | 61.45 |
| H | 5.32 | 5.26 |

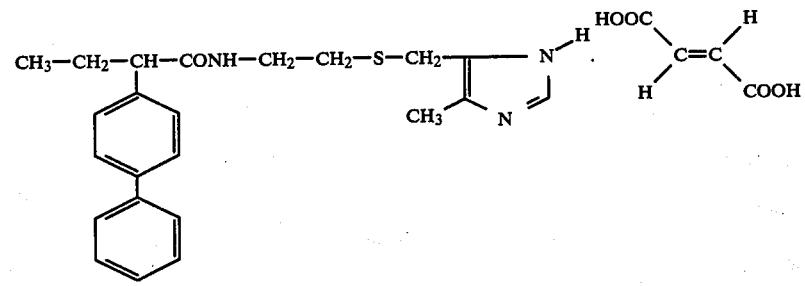

| Elementary analysis | Calculated % | Found % |
|---|---|---|
| N | 10.96 | 11.05 |

The compound of formula (15) is salified with fumaric acid according to the method described in Example 2 and the following derivative is obtained:

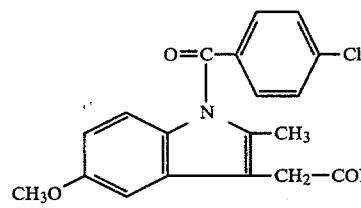

The compound has general formula $C_{30}H_{31}N_4O_7Cl\ S$ and molecular weight 627.11. It appears as odourless, cream-coloured microcrystalline powder, having melting point 169°–172° C. with decomposition. On thin layer chromatography, carried out as above described, it shows two spots: one corresponding to the compound of formula (15) having Rf about 0.56 and the second, corresponding to fumaric acid, at the starting point with Rf=0.0.

The salt is soluble in N,N-dimethylformamide, pyridine, very slightly soluble in ethanol, practically insoluble in acetone, chloroform and water.

| Elementary analysis | Calculated % | Found % |
|---|---|---|
| C | 57.45 | 57.63 |
| H | 4.98 | 5.06 |
| N | 8.93 | 9.01 |

N.M.R. (90 MHz) spectrum (DMSO, δ): 2.15 (s, 3H, $CH_3$); 2.28 (s, 3H, $CH_3$); 2.40–2.70 (m, 2H, $CH_2$); 3.3 (q, 2H, $CH_2$); 3.56 (s, 2H, $CH_2$); 3.70 (s, 2H, $CH_2$); 3.8 (s, 3H, O—$CH_3$); 6.66 (s, 2H, CH=CH); 6.7–8 (m, 8H, aromatic H); 8.25 (m, 1H, NH); 9.7 (s, 3H, NH, COOH).

(g) Compound of formula (A) wherein $R_1$=H, $R_2$=2-hydroxy-5-(2.4-difluorophenyl)benzoil [acylic radical of 2-hydroxy-5-(2.4-difluorophenyl)-benzoic acid (diflunisal)].

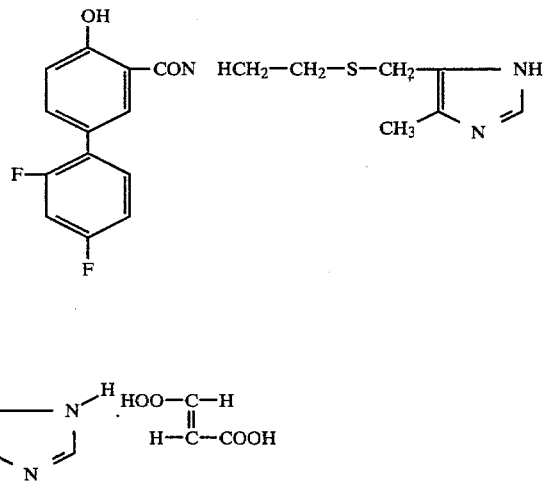

The compound has general formula $C_{20}H_{19}N_3O_2F_2S$ and molecular weight 403.445. It appears as white microcrystals having melting point 191°–193° C.

| Elementary analysis | Calculated % | Found % |
|---|---|---|
| C | 59.54 | 59.27 |
| H | 4.74 | 4.61 |
| N | 10.41 | 10.58. |

N.M.R. (90 MHz) spectrum (DMSO, δ): 2.13 (s, 3H, $CH_3$); 2.40–2.85 (m, 2H, $CH_2$); 3.35–3.70 (m, 2H, $CH_2$); 3.70 (s, 2H, $CH_2$); 6.9–8.2 (m, 7H, aromatic H).

The compounds according to the present invention were the object of pharmacological trials which confirmed the therapeutic ground of these compounds. Particularly, as mere example, the compounds of formula (1) and (4) showed an important antiinflammatory activity without any gastrodamaging effect in the treatment of oedema caused by carrageenin in female rat. The results of such pharmacological trials are collected in the following tables and compared with the results relative to phenylbutazone.

TABLE 1

Antiinflammatory Activity
Subplantar Oedema by carrageenin in Wistar Female Rat

| Treatment | Dose mg/kg p.o. | Weight g. | Basic m̄ | Volume of the leg | | | | | Area Absolute value | % inhibition in comparison with the control |
|---|---|---|---|---|---|---|---|---|---|---|
| | | | | 1 h.m̄ | 2 h.m̄ | 3 h.m̄ | 4 h.m̄ | 5 h.m̄ | | |
| Control | — | 199 ± 4.8 | 26.7 | 34.1 | 42.1 | 44.9 | 44.3 | 46.2 | 253.4 | |
| Phenylbutazone | 100 | 196 ± 5.0 | 26.4 | 29.3 | 32.0 | 32.0 | 34.3 | 35.4 | 100.2 | 60.0 |
| Compound of Formula 1 | 100 | 201 ± 6.1 | 26.5 | 29.0 | 34.1 | 34.1 | 36.1 | 40.0 | 129.8 | 48.0 |

TABLE 2

| | GASTRODAMAGING ACTIVITY WISTAR RAT | | |
|---|---|---|---|
| Treatment | Dose mg/kg p.o. | Weight g. | x̄ (average) mm. ulcer |
| Control | — | 199 ± 4.8 | 0.1 ± 0.1 |
| Compound of Formula 1 | 100 | 201 ± 6.1 | 0.2 ± 0.2 |

TABLE 3

| | Antiinflammatory Activity Subplantar Oedema by Carrageenin in Wistar Female Rat | | | | | | | | | |
|---|---|---|---|---|---|---|---|---|---|---|
| | | | | | | | | | Area | |
| Treatment | Dose mg/kg p.o. | Weight g. | Basic m̄ | Volume of the leg | | | | | absolute value | % inhibition in comparison with the control |
| | | | | 1 h. m̄ | 2 h. m̄ | 3 h. m̄ | 4 h. m̄ | 5 h. m̄ | | |
| Control | — | 199 ± 4.8 | 26.7 | 34.1 | 42.1 | 44.9 | 44.3 | 46.2 | 253.4 | |
| Phenylbutazone | 100 | 196 ± 5.0 | 26.4 | 29.3 | 32.0 | 32.0 | 34.3 | 35.4 | 100.2 | 60.0 |
| Compound of Formula (4) | 100 | 199 ± 5.8 | 25.7 | 28.2 | 31.1 | 32.1 | 34.4 | 35.9 | 109.6 | 56.0 |

TABLE 4

| | GASTRODAMAGING ACTIVITY WISTAR FEMALE RAT (n = 10) | | |
|---|---|---|---|
| Treatment | Dose mg/kg p.o. | Weight g. | x̄ (average) mm. ulcer |
| Control | — | 199 ± 4.8 | 0.1 ± 0.1 |
| Compound of formula (4) | 100 | 199 ± 5.8 | 1.0 ± 0.5 |

The compounds according to the present invention can be used in all the foreseeable pharmaceutical forms which are compatible with their characteristics, eventually mixed with usual components of pharmaceutical compositions and also in union with other active ingredients.

What I claim is:

1. A derivative of 4-methyl-5-[(2-aminoethyl)-thiomethyl]-imidazole of the formula:

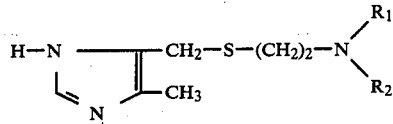

wherein $R_1$ is —H, —$CH_3$ or —$C_2H_5$, wherein $R_2$ is an acylic radical of an antiinflammatory acid selected from the group consisting of indomethacin, diflunisal, flurbiprofen, indoprofen, 4-diphenylyl-ethyl-acetic acid, ibuprofen, naproxen, suprofen, ketoprofen and salicylic acid and wherein $R_1$ can equal $R_2$, or a physiologically acceptable salt thereof.

2. Derivative according to claim 1 wherein said salt is of an acid selected from the group consisting of hydrochloric acid and fumaric acid.

3. Derivative according to claim 1 and wherein said derivative is 2-(p-isobutylphenyl)-propionyl-amide of 4-methyl-5-[(2-aminoethyl)-thiomethyl]-imidazole.

4. Derivative according to claim 1 wherein said derivative is (+) 6-methoxy-α-methyl-2-naphthalen-acetyl-amide of 4-methyl-5-[(2-aminoethyl)-thiomethyl]-imidazole.

5. Derivative according to claim 1 wherein said derivative is 2-(3-benzoylphenyl)-propionyl-amide of 4-methyl-5-[(2-aminoethyl)-thiomethyl]-imidazole.

6. Derivative according to claim 1 wherein said derivative is 2-hydroxy-benzoyl-amide of 4-methyl-5-[(2-aminoethyl)-thiomethyl]-imidazole.

7. Derivative according to claim 1 where said derivative is 4-diphenylylethylacetyl-amide of 4-methyl-5-[(2-aminoethyl)-thiomethyl]-imidazole.

8. Derivative according to claim 1 wherein said derivative is 1-(p-chlorobenzoyl)-2-methyl-5-methoxy-indolylacetylamide of 4-methyl-5-[(2-aminoethyl)-thiomethyl]-imidazole.

9. Derivative according to claim 1 wherein said derivative is 2-hydroxy-5-(2,4-difluorophenyl)-benzoyl-amide of 4-methyl-5-[(2-aminoethyl)-thiomethyl]-imidazole.

10. Derivative according to claim 1 wherein said derivative is [(thenoyl-2)-4-phenyl]-2-propionyl-amide of 4-methyl-5-[(2-aminoethyl)-thiomethyl]-imidazole.

* * * * *